United States Patent [19]
Astrologes

[11] Patent Number: 4,605,802
[45] Date of Patent: Aug. 12, 1986

[54] PRODUCTION OF 1,1,1,3-TETRACHLOROPROPANE

[75] Inventor: Gary W. Astrologes, Hackensack, N.J.

[73] Assignee: Halocarbon Products Corp., Hackensack, N.J.

[21] Appl. No.: 364,175

[22] Filed: Apr. 1, 1982

[51] Int. Cl.$^4$ ............................................. C07C 17/28
[52] U.S. Cl. .................................................. 570/257
[58] Field of Search ......................................... 570/257

[56] References Cited

U.S. PATENT DOCUMENTS

| | | |
|---|---|---|
| 2,658,930 | 11/1953 | Thompson. |
| 3,471,579 | 10/1969 | Kubicek ............................. 570/257 |
| 3,641,170 | 2/1972 | Nakamaye et al. ................ 570/257 |
| 4,243,607 | 1/1981 | Takamizawa et al. ............. 570/257 |

FOREIGN PATENT DOCUMENTS

| | | | |
|---|---|---|---|
| B 36503 | 10/1956 | Fed. Rep. of Germany ...... | 570/257 |
| 2548625 | 4/1974 | Fed. Rep. of Germany ...... | 570/257 |
| 20692 | 2/1966 | Japan .................................. | 570/257 |
| 340812 | 10/1959 | Switzerland ....................... | 570/257 |

OTHER PUBLICATIONS

T. Asahara, M. Seno, and T. Sato, Kogyo Kagaku Zasshi, 74 (11), 2288 (1971).
T. Asahara and T. Sato, Kogyo Kagaku Zasshi, 74, 703 (1971).
Starks, "Free Radical Telomerization", Academic Press 1974, Chapter 5.
Starks', "Free Radical Telomerization" (1974), pp. 108–119.

Primary Examiner—Charles F. Warren
Assistant Examiner—Joseph A. Boska
Attorney, Agent, or Firm—Sprung Horn Kramer & Woods

[57] ABSTRACT

In the reaction of carbon tetrachloride with ethylene in the presence of a catalyst comprising a phosphite ester and an iron-containing material to produce 1,1,1,3-tetrachloropropane, the improvement which comprises employing powdered iron as the iron-containing material. Thereby the carbon tetrachloride is converted in large amount and with high selectivity to the desired product. The reaction proceeds well even under milder conditions than with the catalysts of the prior art.

12 Claims, No Drawings

PRODUCTION OF 1,1,1,3-TETRACHLOROPROPANE

The present invention relates to an improvement in the known process of reacting carbon tetrachloride with ethylene in the presence of catalyst to produce 1,1,1,3-tetrachloropropane.

T. Asahara et al in two articles in volume 74 of Kogyo Kagaku Zasshi (1971) at pages 703 to 705 and 2288 to 2290 teach the reaction of carbon tetrachloride with ethylene in the presence of a phosphite ester and metal salts, particularly iron chloride, to effect telomerization. The reactions proceed to various degrees, producing 1,1,1,3-tetrachloropropane along with relatively large amounts of higher telomers, as follows:

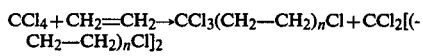

wherein n is mostly 1 with significant amounts of n as 2 and 3.

T. Asahara et al in a later article in Bulletin of the Chemical Society of Japan Vol. 46 (1973) pages 3193–7 discloses a similar reaction using N-chloroalkylamines as telomerization catalysts. Small amounts of iron, copper and their salts were added and on page 3196 near the top of the first column the authors state "The addition of iron did not affect the reactivity of N-chloroalkylamines."

U.S. Pat. No. 2,658,930 discloses a mixture of iron metal, water, and air will slowly catalyze the addition of carbon tetrachloride to 1-octene. In the only example of this reaction included, 22 days of reaction gave only 10 g of addition product from 500 g of carbon tetrachloride. The presence of oxygen was cited as necessary for this process, whereas hereinbelow it is shown to be disadvantageous in the instant process.

Starks in Chapter 5 of his book "Free Radical Telomerization" Academic Press 1974 summarizes much of the large amount of earlier work with a variety of catalysts. He explains how iron chloride performs and on page 105 he tabulates initiators, some of which have been summarized hereinabove.

It is an object of the present invention to provide a different catalyst system which permits the reaction to 1,1,1,3-tetrachloropropane to proceed rapidly with high selectivity, yield and efficiency.

In accordance with the present invention carbon tetrachloride is reacted with ethylene in the presence of a phosphite ester such as triethylphosphite and powdered iron. If desired, iron salts such as ferric chloride may also be present. Advantageously oxygen is excluded from the vessel in which the reaction is conducted.

The reaction may be carried out at about 70° to 140° C. although about 80° to 110° C. is preferred. The pressure resulting from the vapor pressure of the liquids and the added ethylene may range from about 25 to 500 psig although about 70 to 150 psig is preferred.

The phosphite ester can be used in conventional amounts, e.g. about 0.0005 to 0.1 and preferably about 0.002 to 0.02 mole per mole of carbon tetrachloride. The powdered iron can be of any type although electrolytic iron powder and hydrogen-reduced iron powder are especially useful. The iron powder should be present in at least about 0.001 and preferably at least about 0.01 mole per mole of carbon tetrachloride. Larger amounts are not harmful and unconsumed excess can be employed in further reaction. Small particle size, preferably below about 50 microns, increases the surface per unit weight and favors use of small amounts of iron.

If desired salts such as ferric chloride and/or other initiators can also be added in conventional amounts but are not necessary.

The reaction is advantageously effected by adding the carbon tetrachloride, phosphite and iron powder, plus any other initiators, to a reaction vessel which is thereafter flushed out with a gas such as ethylene or brought to the boiling point to remove any oxygen. The reactor is sealed and the temperature brought to that desired for reaction. Simultaneously the reactor is pressurized with ethylene to the desired level and ethylene is periodically introduced to maintain the pressure within the desired range. Finally, the internal pressure is permitted to fall as ethylene is consumed and then the temperature is also optionally permitted to fall to about room temperature. The liquid products are removed and fractionated, the solid unreacted iron remaining behind for use in another cycle possibly with some make-up iron powder.

Between runs the reactor may be rinsed with a solvent such as methylene chloride, acetone and/or water, and the like to remove inhibiting residues but under the preferred conditions where ferric chloride is not added this may not be necessary.

The invention will now be further described in the following illustrative examples wherein all parts are by weight unless otherwise expressed.

EXAMPLE 1

Run 14: To a clean 1200 cc stainless steel pressure vessel at room temperature were added 947. g of carbon tetrachloride ($CCl_4$), 5.5 g of triethyl phosphite ($(EtO)_3P$), 1.174 g of ferric chloride ($FeCl_3$), and 7.5 g of electrolytic iron powder. The vessel was sealed and alternately evacuated to 70 to 90 mm of mercury and pressurized to 155 pounds per square inch (psig) with ethylene 3 times, thereby removing any significant amount of oxygen from the reactor. In the process 46 g of carbon tetrachloride was distilled out of the reactor leaving 901.4 g behind. The reactor was then heated to 95° C. and shaken on a vibrating table to mix the reactants. As the reactor temperature neared 95° C. the vessel was pressured to 110 psig with ethylene. Ethylene was then added as necessary to keep the pressure between 90 and 110 psig. After 11.3 hours at 95° C. the rate of ethylene uptake by the reactor had dropped to 12% of its maximum value indicating that the reaction had slowed considerably. The reactor was then cooled to room temperature and the product mixture was analyzed by gas chromatography and shown to consist by weight of 75.9% 1,1,1,3-tetrachloropropane, 21.2% unreacted carbon tetrachloride, 2.4% second addition products, and 0.5% other products, corresponding to a 79% conversion of the $CCl_4$ and a 96.3% yeild of the desired product. The liquid product mixture was poured out of the reactor, leaving unreacted iron powder in the reactor.

Run 15: The reactor was shaken with 70 ml of methylene chloride ($CH_2Cl_2$) to dissolve any deposits sticking on its walls. The methylene chloride was poured out of the reactor and evaporated to give 0.66 g of solids. The reactor was now ready to run again. A fresh charge of similar amounts of carbon tetrachloride, triethyl phosphite and ferric chloride was added but no new iron powder. The reactor was run as before resulting in an 84% conversion of the carbon tetrachloride and a 96.3% yield of 1,1,1,3-tetrachloropropane.

EXAMPLE 2

Run 20: This was run as in Example 1 in the same reactor except that no ferric chloride was added. To the reactor were added 952.6 g of carbon tetrachloride, 5.4 g of triethyl phosphite and 7.5 g of a commercial grade of hydrogen-reduced iron powder. Removal of any oxygen was performed as in Example 1, leaving 856.7 g of $CCl_4$ in the reactor. As before the reactor was shaken, heated to 95° C., and pressurized to 90 to 110 psig with ethylene. After 11.1 hours at 95° C. the reactor was cooled and the liquid products (937.5 g) were poured out, leaving much unreacted iron powder behind. The product mixture contained 90.8% 1,1,1,3-tetrachloropropane, 5.0% unreacted carbon tetrachloride, 3.7% second addition products, and 0.5% other products, corresponding to a 95% conversion of the carbon tetrachloride and a 95.6% yield of tetrachloropropane.

Run 21: To this reactor without any cleaning was added a new charge of 947.2 g of carbon tetrachloride and 5.3 g of triethyl phosphite but no new iron powder. After degassing (902.5 g of carbon tetrachloride left in the reactor) followed by 11.1 hours of shaking at 95° C. under 90–110 psig of ethylene pressure, the product mixture (920. g) analyzed as 89.5% tetrachloropropane, 6.5% unreacted carbon tetrachloride, 3.5% second addition products and 0.5% other products, corresponding to a 94% conversion of carbon tetrachloride and a 95.7% yield of tetrachloropropane.

EXAMPLE 3

Run 32: To a clean 9 gallon Monel pressure vessel was added 27,200 g of carbon tetrachloride which was degassed by refluxing. The vessel was then pressurized to 30 psig with ethylene. A solution of 495 g of benzoyl peroxide in 13,600 g of degassed $CCl_4$ was slowly added to the 90° C. reactor over the next 30 hours during which the ethylene pressure was raised from 28 to 38 psig. The reactor contents were shown by gas chromatography to consist of 62.8% unreacted $CCl_4$, 31.9% 1,1,1,3-tetrachloropropane, 3.4% second addition products and 1.9% other products, corresponding to a 37% conversion of the $CCl_4$ and an 85.7% yield of the desired product. There was a relatively large 9.3% yield of the undesired second addition products even though the low conversion and ethylene pressure minimize this side reaction.

Other runs were conducted under substantially the same conditions and their particulars and results, along with those for the preceeding five runs, are set forth in the table which follows. All runs were in a clean reactor at 90 to 110 psig unless otherwise indicated. Mole % of catalyst is based on $CCl_4$ used; % yield is based on $CCl_4$ converted.

TABLE

| Run | Grams $CCl_4$ | Mole % $(EtO)_3P$ | Mole % $FeCl_3$ | Mole % Fe Powder | Time (hrs) | Temp (°C.) | TCP Yield (%) | $CCl_4$ Conv. (%) | Comments |
|---|---|---|---|---|---|---|---|---|---|
| 1 | 11930 | 0.54 | 0.12 | — | 12.2 | 95 | 95.5 | 43 | |
| 2 | 11740 | 0.55 | 0.12 | — | 14.1 | 95 | 95.9 | 35 | |
| 3 | 11700 | 0.56 | 0.12 | — | 15.0 | 95 | 96.1 | 34 | |
| 4 | 11895 | 0.55 | 0.12 | — | 14.8 | 95 | 95.8 | 24 | |
| 5 | 904.1 | 0.55 | 0.115 | — | 12.7 | 95 | 95.5 | 43 | |
| 6 | 894.4 | 0.59 | 0.120 | — | 14.7 | 95 | 95.4 | 47 | |
| 7 | 900.0 | 0.58 | 0.120 | — | 14.9 | 95 | 95.1 | 48 | |
| 8 | 905.5 | 0.56 | 0.124 | — | 16.0 | 95 | 96.1 | 46 | (1) |
| 9 | 885.6 | 0.575 | 0.122 | 2.33 | 11.0 | 95 | 96.1 | 83 | (2) |
| 10 | 861.0 | 0.61 | 0.125 | 2.37 | 22.6 | 85 | 95.9 | 87 | (2) |
| 11 | 874.9 | 0.58 | 0.122 | .47 | 15.1 | 95 | 95.7 | 61 | (2) |
| 12 | 898.2 | 0.55 | 0.122 | 1.82 | 10.1 | 95 | 95.6 | 45 | (2,3,4,6) |
| 13 | 894.2 | 0.59 | 0.119 | — | 11.2 | 95 | 96.3 | 84 | (2,3,5,6) |
| 14 | 901.4 | 0.565 | 0.123 | 2.3 | 11.3 | 95 | 96.3 | 79 | (2) |
| 15 | 898.9 | 0.57 | 0.124 | — | 11.2 | 95 | 96.3 | 84 | (3,6,7) |
| 16 | 925.7 | 0.55 | 0.114 | 2.2 | 11.2 | 95 | 96.3 | 87 | (8) |
| 17 | 896.0 | 0.59 | 0.122 | — | 14.9 | 95 | 95.9 | 78 | (3,6,7) |
| 18 | 905.2 | 0.55 | 0.124 | 2.25 | 15.6 | 95 | 96.3 | 86 | (9) |
| 19 | 892.0 | 0.58 | 0.122 | — | 11.1 | 95 | 96.4 | 53 | (3,6,7) |
| 20 | 856.7 | 0.58 | — | 2.41 | 11.1 | 95 | 95.6 | 95 | (8) |
| 21 | 902.5 | 0.54 | — | — | 11.1 | 95 | 95.7 | 94 | (3,6) |
| 22 | 906.3 | 1.13 | 0.487 | — | 16.0 | 95 | 97.8 | 68 | |
| 23 | 904.5 | 0.56 | 0.48 | — | 11.7 | 95 | 89.9 | 90 | (10) |
| 24 | 864.9 | 0.59 | — | 2.36 | 6.5 | 120 | 93.3 | 99 | (8) |
| 25 | 902.2 | 0.56 | — | — | 6.7 | 120 | 88.8 | 75 | (3,6) |
| 26 | 903.6 | 0.57 | — | 2.26 | 6.7 | 120 | 93.2 | 99 | (8) |
| 27 | 894.9 | 1.14 | — | — | 11.6 | 120 | 94.3 | 99.6 | (3,6,11) |
| 28 | 873.7 | 0.59 | 0.013 | 2.23 | 11.0 | 95 | 95.2 | 88.5 | (8) |
| 29 | 901.6 | 0.555 | 0.012 | 2.26 | 5.5 | 110 | 94.9 | 81 | (8) |
| 30 | 890.0 | 0.57 | — | — | 5.5 | 110 | 95.4 | 87 | (3,6) |
| 31 | 860.8 | 0.59 | — | 2.40 | 6.2 | 120 | 94.0 | 99 | (8,12) |

TABLE-continued

| Run | Grams CCl$_4$ | Mole % (EtO)$_3$P | Mole % FeCl$_3$ | Mole % Fe Powder | Time (hrs) | Temp (°C.) | TCP Yield (%) | CCl$_4$ Conv. (%) | Comments |
|---|---|---|---|---|---|---|---|---|---|
| 32 | 40,800 | — | — | — | 30. | 90 | 85.7 | 37 | (13,14) |

COMMENTS
1 14.9 g of 316 stainless steel powder added.
2 Used reagent-grade electrolytic iron powder.
3 Iron powder left in reactor from previous reaction.
4 Reaction stopped using ethylene at 10.1 hrs.
5 Reactor rinsed with acetone before loading new reactants.
6 Reactor not thoroughly cleaned after previous reaction.
7 Reactor rinsed with CH$_2$Cl$_2$ before loading new reactants.
8 Used commercial hydrogen-reduced powder.
9 Used commercial iron powder (not hydrogen-reduced).
10 Run at 450 psig.
11 0.57 moles of the phosphite was added initially and 0.57 moles was added 8.3 hrs. after the reaction began.
12 Tributyl phosphite was used instead of (EtO)$_3$P.
13 0.77 mole % benzoyl peroxide was added to the CCl$_4$ intermittently. The reaction was run at 28-38 psig.
14 A 9.3% yield of the 2nd addition by-product was also obtained.

Analysis of these runs shows that operation in accordance with the invention compared with peroxide-initiated reaction results (Run 32, Example 3) in much higher conversions and less by-product production, i.e. second addition products.

Runs 1 to 4, outside the present invention because of the absence of iron powder but under otherwise similar conditions and proportions, show that at best a 43% conversion was obtained in a large reactor freshly cleaned out with acetone and water. Subsequent reactions leave a residue on the reactor walls that increasingly reduces the effectiveness of the catalyst with the conversion dropping to 24% for the fourth reaction.

Runs 5,6 and 7 show similar 43 to 48% conversions in a smaller clean reactor using the triethyl phosphite and ferric chloride in the standard amounts. Run 8 shows adding a relatively large amount of 316 stainless steel powder to this catalyst mixture has no noticeable effect (46% conversion). Runs 9 and 10 show the conversion increases to 83 and 87% when reagent grade electrolytic iron powder is present in the reactor along with the FeCl$_3$ and (EtO)$_3$P. At 85° C. the reaction takes twice as long as at 95° C. As in the Japanese references the ferric chloride can be present as either the anhydrous or the hexahydrate salt.

Run 11 shows that a small amount of iron powder gives a conversion (61%) between that achieved using larger amounts of iron powder (83-87%) and those using none at all (Runs 1,5-7). Run 12 was conducted without cleaning the residues out of the reactor left from Run 11. Run 12's lower conversion (45%) shows that even with additional iron powder added to bring the iron content up to that of Run 9 or 10, this catalyst system suffers from the same drawback as before; the reaction is inhibited by the residues from the previous reaction. However, unlike the (EtO)$_3$P or FeCl$_3$, excess unreacted powdered iron can be reused if the inhibiting residues are washed out of the reactor.

Run 13 shows that rinsing the reactor with acetone after Run 12 brought the conversion back up to 84% without adding any fresh powdered iron. Runs 14 and 15 (Example 1) show that CH$_2$Cl$_2$ will also wash away any inhibiting deposits on the reactor walls.

Runs 16 and 17 show a commercial grade of hydrogen-reduced iron behaves similarly to the more expensive reagent-grade electrolytic iron previously used. Runs 18 and 19 show an even cheaper and coarser grade of commercial iron powder (not hydrogen-reduced) reacts more slowly and gave only a 53% conversion on reuse with CH$_2$Cl$_2$ washing of the reactor walls.

Run 20 (Example 2) shows that the FeCl$_3$ is not necessary when iron powder is present. In fact, a higher conversion (95%) is obtained without it. This iron powder-triethyl phosphite catalyst mixture also has the advantage of not leaving an inhibiting residue in the reactor. Run 21 (Example 2) shows that after just pouring out the liquid products from Run 20, leaving the heavy powdered iron at the bottom of the reactor and adding only fresh CCl$_4$ and (EtO)$_3$P, an excellent conversion of 94% was obtained.

An alternative way to increase the conversion of this reaction without using iron powder is to increase the amount of ferric chloride and triethyl phosphite used. Run 22 shows that even using double the normal amount of phosphite and four times the normal amount of ferric chloride gave only a modest increase to 68% conversion from the 43 to 48% achieved in Runs 5, 6 and 7. The use of the iron powder-phosphite catalyst is not only cheaper but gave higher conversions (95%). Raising the ethylene pressure in addition to increasing the amounts of FeCl$_3$ and (EtO)$_3$P is another alternative, but it took 4½ times the normal pressure and four times the amount of ferric chloride to bring the conversion up to 90% (Run 23). This has the disadvantages of requiring more expensive equipment with higher pressure ratings as well as lowering the yield from 95-96% down to 90%. A high conversion is desirable to save the costs of recovering unreacted CCl$_4$ by distillation and for other reasons.

Runs 24 and 26 show that this reaction can be run at higher temperatures with fresh iron powder and phosphite ester to 99% conversion in only 6.5 hours. However, the yield decreased by a few percent and Run 25 shows that when the iron powder used a second time, it had lost a significant amount of its activity. Run 27 shows that one way to offset the loss of iron activity upon reuse at 120° C. is to add a second portion of (EtO)$_3$P to the reactor when the first portion has been consumed.

In reactions using fresh iron powder and no ferric chloride in their catalyst mixture such as reactions 20,24 and 26, little or no reaction occurs at first until the mixture has been heated for a period ranging from 20 minutes to 2 hours. If this is not desired, Runs 28 and 29 show that the presence of roughly 0.012 mole % or more FeCl$_3$ will cause the reaction to start up upon being heated without this delay. Presumably the delay is caused by the need to form a small amount of iron salt from the iron powder to act as intermediates in the initiation of the desired reaction. Experiment 30 shows that this small amount of added ferric chloride did not decrease the conversion when the reaction was repeated in the same reactor without any solvent rinsing. This is in contrast with the lowered conversion seen in Run 12 where 10 times as much ferric chloride were used in two successive reactions.

Run 31 shows that other alkyl phosphites used in the initiator mixture will also work. This reaction was carried out similar to Run 24 except that the triethyl phosphite was replaced with tributyl phosphite. Similar high yields and conversions were obtained with either phosphite.

It is noted that the temperatures and pressures are considerably lower than in the Japanese references noted hereinabove, and these represent advantages in accordance with the invention. Since the references were interested primarily in the initial rate of reaction, they generally terminated their reactions after 1 or 2 hours, which is not commercially practical. Therefore direct side-by-side comparison with their references is not possible; instead various runs were included employing their initiators but under the same conditions as herein preferred (Runs 1–7).

It will be understood that the specification and examples are illustrative but not limitative of the present invention and that other embodiments within the spirit and scope of the invention will suggest themselves to those skilled in the art.

What is claimed is:

1. A process comprising reacting carbon tetrachloride with ethylene in the presence of a catalyst comprising a phosphite ester and powdered iron thereby to produce 1,1,1,3-tetrachloropropane.

2. The process according to claim 1, wherein ferric chloride is additionally present.

3. The process according to claim 1, wherein the reaction is effected in the substantial absence of oxygen.

4. The process according to claim 1, wherein the phosphite ester is triethyl phosphite.

5. The process according to claim 1, wherein the phosphite ester is tributyl phosphite.

6. The process according to claim 1, wherein at the end of the reaction the liquid products are removed from the reaction vessel for recovery of 1,1,1,3-tetrachloropropane leaving solid iron powder in the reaction vessel, and additional phosphite, carbon tetrachloride and ethylene are added to effect further reaction.

7. The process according to claim 6, wherein between successive reactions the reaction vessel is rinsed with a solvent.

8. The process according to claim 7 wherein the solvent is methylene chloride.

9. The process according to claim 7, wherein the solvent is acetone.

10. The process according to claim 1, wherein the reaction is effected at about 70° to 140° C. and from about 25 to 500 psig.

11. The process according to claim 1, wherein the iron powder is employed in excess of about 0.001 mole per mole of carbon tetrachloride.

12. A process according to claim 6, wherein the phosphite ester is triethyl phosphite and the reaction is effected in the substantial absence of oxygen at about 70° to 140° C. and from about 25 to 500 psig, the iron powder initially being provided in excess of about 0.001 mole per mole of carbon tetrachloride and additional iron powder being added between successive runs to make up for consumed iron thereby to produce 1,1,1,3-tetrachloropropane.

* * * * *